United States Patent [19]
Namiki

[11] Patent Number: 5,617,313
[45] Date of Patent: Apr. 1, 1997

[54] IMAGE DISPLAYING METHOD

[75] Inventor: Fumihiro Namiki, Kawasaki, Japan

[73] Assignee: Fujitsu Limited, Kawasaki, Japan

[21] Appl. No.: 37,373

[22] Filed: Mar. 26, 1993

[30]     Foreign Application Priority Data

Apr. 22, 1992 [JP] Japan .................................. 4-103164

[51] Int. Cl.⁶ .................................................. G06F 15/00
[52] U.S. Cl. ......................................................... 395/263
[58] Field of Search ..................... 364/413.13, 413.22,
364/413.23; 250/491.1, 327.2, 587, 580,
590; 395/102, 139, 100, 135, 134; 382/18,
51, 299, 282, 283

[56]                    References Cited

U.S. PATENT DOCUMENTS

| | | | |
|---|---|---|---|
| 4,999,497 | 3/1991 | Funahashi et al. ............... | 250/587 |
| 5,028,782 | 7/1991 | Nakajima ............................ | 250/327.2 |
| 5,042,077 | 8/1991 | Burke .................................. | 382/51 |
| 5,049,746 | 9/1991 | Ito ....................................... | 250/327.2 |
| 5,260,873 | 11/1993 | Hishinuma ......................... | 364/413.22 |
| 5,283,736 | 2/1994 | Nagatsuka et al. ................ | 364/413.13 |

*Primary Examiner*—Gail O. Hayes
*Assistant Examiner*—Felicia Ives
*Attorney, Agent, or Firm*—Staas & Halsey

[57]                    ABSTRACT

The present invention relates to a method for displaying images such as radiation images on a display apparatus such as, for example, a cathode-ray tube. This method is intended to obtain conversion information for converting first pixel data to second pixel data which is suited to display in accordance with pixel data corresponding to a partial area of the image to be displayed. Additionally, this method enables display of an image with a high contrasts resolution when only a partial image corresponding to a partial area of the image is displayed.

13 Claims, 14 Drawing Sheets

Overall display

Overall histogram

Lookup table for CRT display

Magnified display of the lung thorax (a) alone

Histogram of area (a) alone

Lookup table for CRT display

Fig. 5(A) Magnified display of the heart (b) alone
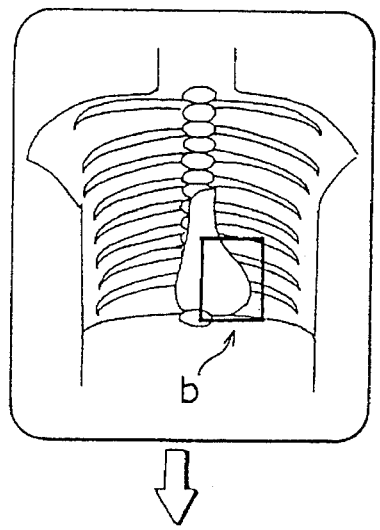
Fig. 5(B) Histogram of area (b) alone
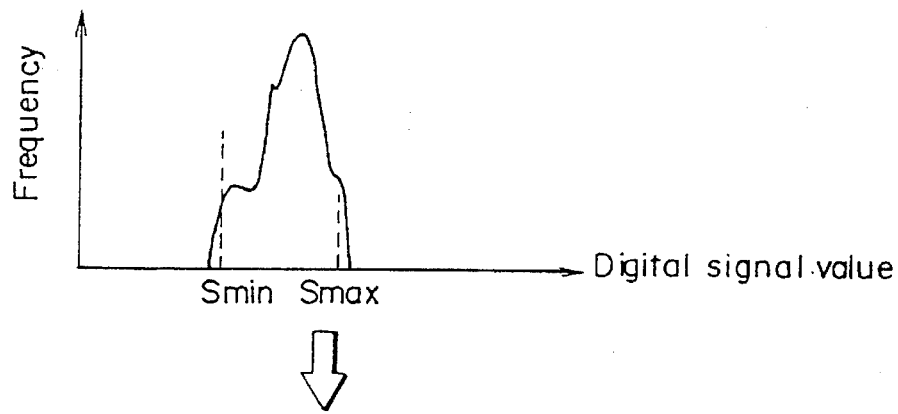
Fig. 5(C) Lookup table for CRT display
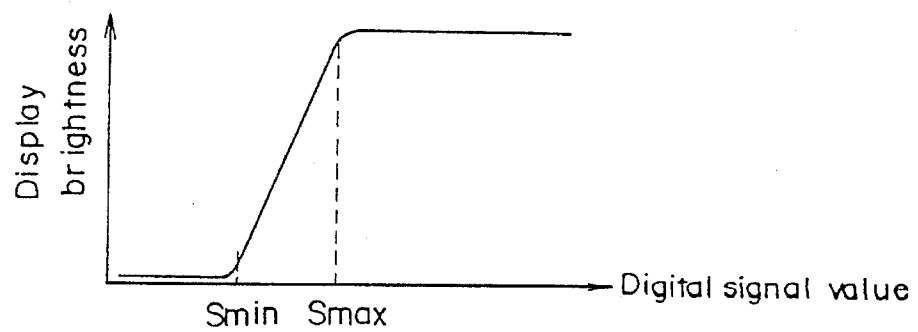

Fig. 16(A)
Histogram of overall image
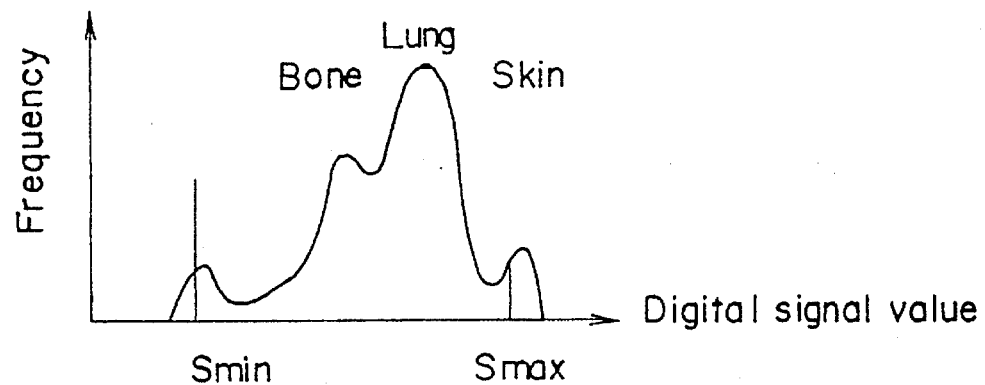
Fig. 16(B)
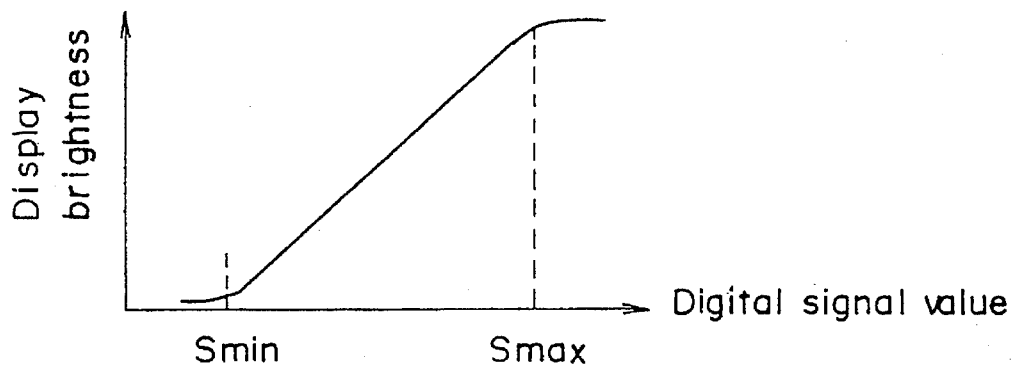

IMAGE DISPLAYING METHOD

BACKGROUND OF THE INVENTION

1. Field of the Invention

The present invention relates to a method for displaying images such as, for example, radiation images on a displaying apparatus such as a cathode-ray tube (CRT) and more particularly to a method of gradation processing for displaying the images of partial areas of the above described images.

2. Description of the Related Art

Conventionally, radiation images such as, for example, X-ray images have often been used for diagnosing diseases and other diagnostic applications. In the case of X-ray images, for example, X-rays which have passed through a subject are irradiated onto a layer of phosphorescence fluorescent material (fluorescent screen); X-rays are converted to visible rays; a latent image is formed by irradiating these visible rays onto a silver chloride film; and an X-ray image is obtained by developing this silver chloride film. Those X-ray images thus obtained have been used in diagnoses of diseases and other diagnostic applications.

Lately, methods by which digital image information obtained from X-ray CT (computer tomography), MRI and X-ray II camera is displayed on the cathode-ray tube (CRT) and stored in magnetic storage media or the like has been widely utilized. Also in the field of radiation photography where such conventional silver chloride films as described above have been used, those systems capable of digitizing image information and displaying it on the CRT have been proposed. One of these systems is a method which uses an accelerated phosphorescence fluorescent material. A basic system which employs this accelerated phosphorescence fluorescent material is disclosed in detail in the U.S. Pat. No. 3,859,527.

The following paragraphs describe in detail a system which uses the accelerated phosphorescence florescent material.

A phosphorescence fluorescent material used in this system is called an accelerated phosphorescence fluorescent material which accumulates energies of radiations such as X-rays when the X-rays are irradiated thereupon. The state of this accumulation is relatively stable and can be maintained for a long period of time. When a first beam serving as an excitation beam is irradiated-onto the phosphorescence fluorescent material which stores the energies of radiations, an accelerated phosphorescence light with an intensity corresponding to the accumulated energy is radiated as a second beam. In this case, not only visible rays but also those rays with a wide range of wavelength from infrared rays to ultraviolet rays are used. The type of ray, however, differs with the type of fluorescent material to be used. The second beam is variously available in the range from infrared rays to ultraviolet rays. This difference depends on the type of phosphorescence fluorescent material to be used.

An X-ray photography system has been materialized for practical use to obtain radiation image information by irradiating and receiving radiations which have passed through a subject such as a human body onto the above described accelerated phosphorescence fluorescent material while making use of the characteristics of the accelerated phosphorescence fluorescent material.

Specifically, an accelerated phosphorescence light is generated by scanning a plate or sheet made of accelerated phosphorescence fluorescent material, which stores X-ray image information of a subject, with an excitation beam such as a laser beam. This accelerated phosphorescence light is condensed by a photoelectric converter to obtain electrical signals proportional to the intensities of accumulated radiations. Subsequently, the electrical signals are processed for imaging and a visualized radiation image is obtained by printing the image on a silver chloride film or displaying it on the CRT.

FIG. 15 is an approximate structure of the conventional radiation image information reader.

The accelerated phosphorescence fluorescent panel 3-1 on which an X-ray image is accumulated and stored is transferred (sub-scanning) in the Y direction shown with an arrow, by a precision slide 3-7.

During this transfer (sub-scanning), an excitation beam emitted from an excitation beam source 3-4 such as a gas laser, semiconductor laser or the like is repeatedly reflected and deflected by a scanner 3-5 such as, for example, a galvanometer mirror or a polygon mirror and irradiated onto the accelerated phosphorescence fluorescent panel 3-1 after having passed through an optical system 3-6 such as an fθ lens for correcting the shape of beam. Thereby the accelerated phosphorescence fluorescent panel 3-1 is repeatedly scanned (main scanning) with the excitation beam in the X direction shown with the arrow. Accelerated phosphorescence fluorescent rays which bear the X-ray image accumulated and are stored on the accelerated phosphorescence fluorescent panel 3-1, are radiated from all scanning points. These accelerated phosphorescence rays are condensed through a light guide passage 3-8 consisting of a plurality of optical fibers which are bound together; guided to a photomultiplier 3-9 through an optical filter (not shown) which cuts off the excitation beam and admits the accelerated phosphorescence light; and converted into electric signals.

Electric signals obtained from the photo-multiplier 3-9 are amplified by an initial stage amplifier 3-10 to a most suitable signal level for an A/D converter 3-11. Pixel data which are digitized as signals for each pixel by the A/D converter 3-11 is stored in an image memory 3-12. The range of intensity and the gradation curve are converted for display and sent to a video memory 3-12. Pixel data sent to the video memory 3-14 are converted to display luminance signals and displayed on the CRT 3-16 or outputted as a hard copy on a film (not shown).

FIG. 16 illustrates an example of a method for obtaining the conversion information to be recorded on a lookup table 3-13.

First a histogram of pixel values of image data corresponding to a whole image is obtained, the minimum value (Smin) and the maximum value (Smax) to be displayed are determined within the histogram and a lookup table is prepared by correlating the signal levels and the display brightnesses included between these minimum and maximum values in terms of various shapes of curves (so-called gradation curves). Pixel data read out from the image memory 3-12 is converted by using the lookup table 3-13 (refer to FIG. 15) and sent to the video memory 3-14 whereby an image with an appropriate brightness is displayed on the CRT (cathode-ray tube) 3-16.

In this connection, it has been reported that conventional silver chloride films for use in observation of X-ray images of human bodies such as, for example, 14 inch×14 inch silver chloride films are provided with a resolution of 4000 dots×4000 dots. In contrast, the CRT is usually provided with a resolution of only approximately 1000 dots×1000 dots and even an expensive CRT only provides the resolution of 2000 dots×2000 dots.

In some cases, in an attempt to rectify such insufficient resolution, the overall image is first displayed to check the presence of an abnormal shade or shades when an image obtained from the above described system is displayed on the CRT for observation and diagnosis. Next, the part of the image, with which the user is concerned, is magnified for further minute observation and diagnosis.

However, the CRT is also inferior to conventional silver chloride films the in the display contrast. For example, silver chloride films can represent the gradation of approximately 12 bits=4096 whereas the CRT represents the gradation of only 8 bits=256.

Conventionally, even for magnifying the display of a part, with which the user is concerned, of the image on the CRT, the conversion information which has been obtained to produce an appropriate brightness over the whole image as described above, has been directly used as the lookup table. Therefore only a partial area of the image is magnified and displayed with its own current brightness whether the partial area has a high brightness when the entire image is taken or a low brightness as a whole. In some cases, accordingly, the magnified image of this partial area has appeared with a low contrast resolution.

SUMMARY OF THE INVENTION

An object of the present invention made in view of the above findings is to provide an image displaying method capable of enabling display of an image with high contrast resolution when displaying only a partial image corresponding to a partial area of the image.

An image displaying method according to the present invention to implement the above object, wherein a plurality of first pixel data respectively corresponding to a plurality of pixels which form an image is stored in advance, the first pixel data is read out, second pixel data is obtained by converting the pixel values of the first pixel data to those values for display and an image based on the second pixel data is displayed, comprises the steps of:

(1) Reading the first pixel data corresponding to the partial area of the image, (2) Obtaining conversion information for converting the first pixel data to the second pixel data, in accordance with the first pixel data which has been read, (3) Converting the first pixel data corresponding to the partial area of the image, in accordance with the above conversion information, and (4) Displaying an image corresponding to the above partial area in accordance with the second pixel data.

In this case, the type of the above conversion information in the present invention is not taken up for consideration and the conversion information is available, for example, in terms of conversion formulae and conversion tables.

A preferable method for obtaining the conversion information is to obtain a histogram of pixel values of the first pixel data corresponding to the partial area and the conversion information based on the above histogram. For obtaining the above conversion table, a conversion formula can be obtained and a conversion table can be prepared according to calculation based on this conversion formula or a plurality of conversion tables can be prepared in advance and one of the plurality of conversion tables which have been prepared can be selected in accordance with the above described histogram.

As the above conversion table, for example, a lookup table is adopted. For example, pixel data which has been obtained by reading the radiation image information from the accelerated phosphorescence fluorescent material in which radiation image information is accumulated is used as the first pixel data.

An image displaying method according to the present invention is intended to obtain the conversion information for converting the first pixel data to the second pixel data suited for display in accordance with the pixel data corresponding to a partial area to be displayed. Therefore an image with a high contrast resolution is always displayed when, for example, magnifying and displaying the partial image.

Though the conversion information can be obtained in accordance with, for example, mean values, dispersion or the like of the first pixel data corresponding to the partial area as a method for obtaining the conversion information in accordance with the first pixel data corresponding to the partial area, the most suitable method is to obtain a histogram of pixel values of the first pixel data corresponding to the partial area and the conversion information according to this histogram. If a conversion table is used as the conversion information, a lookup table type conversion table is preferably used. Though the images to be handled in conformity to the present invention are not limited to specific images, the present invention is preferably embodied for processing radiation images which are obtained by using an accelerated phosphorescence fluorescent material.

As described above, the image displaying method according to the present invention is adapted to obtain the conversion information for converting the pixel data to those data for display in accordance with the pixel data corresponding to this partial area. This therefore allows display of an image with a high contrast resolution which can be easily observed even when displaying only the partial area.

BRIEF DESCRIPTION OF THE DRAWINGS

FIG. 5 is a diagram showing an example method for obtaining a lookup table, FIG. 16 is a diagram showing an example method for obtaining the conversion information to be recorded in the lookup table.

DESCRIPTION OF THE PREFERRED EMBODIMENTS

Preferred embodiments of the present invention are described below. The following paragraphs describe the embodiments applied to those systems which employ the accelerated phosphorescence fluorescent material. The present invention does not, however, apply only to the systems which employ the accelerated phosphorescence fluorescent material and would also apply to the display of only a partial area of the image.

Figure 1:
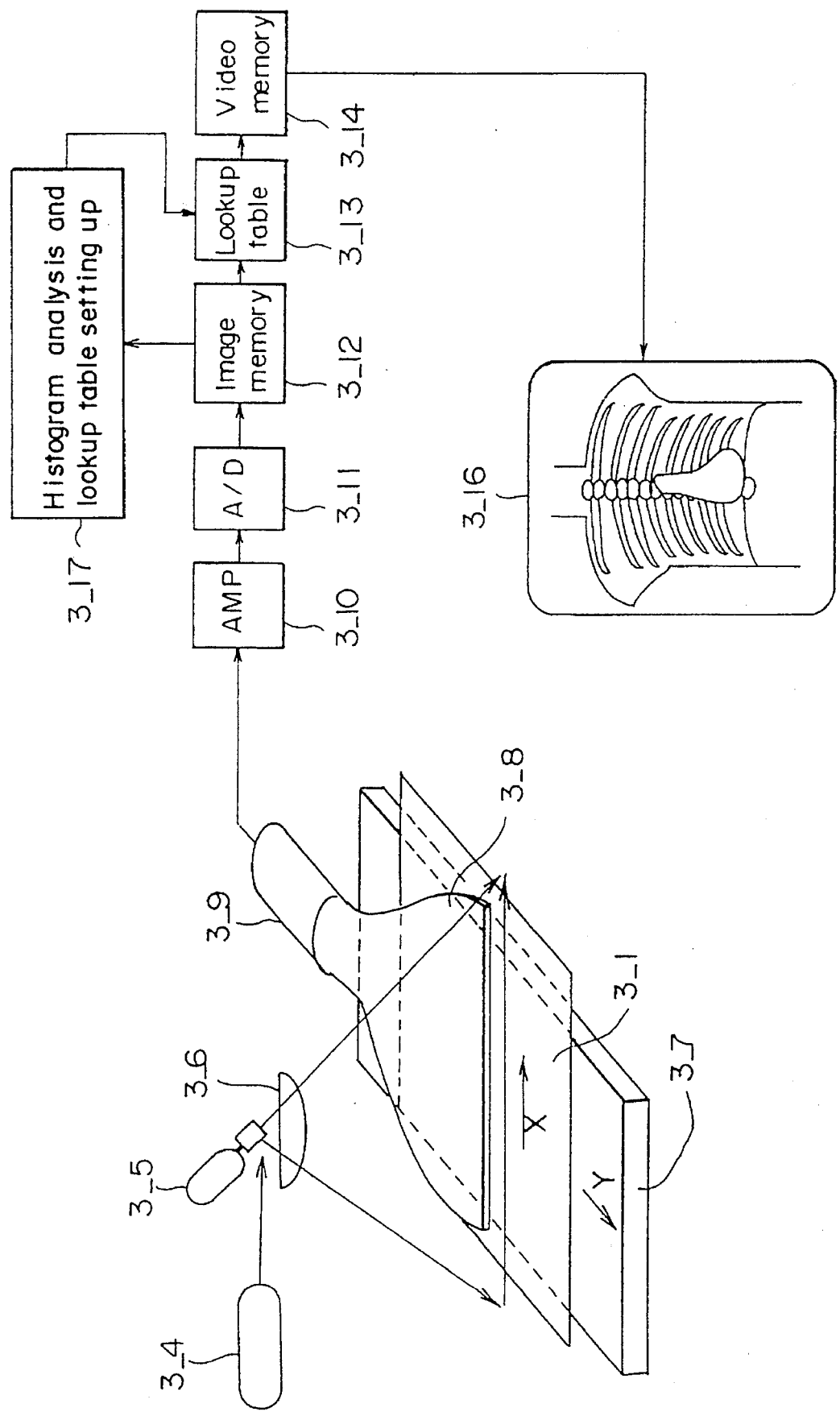
FIG. 1 is an approximate configuration of a radiation image information reader involving the first embodiment of the present invention.
Figure 2:
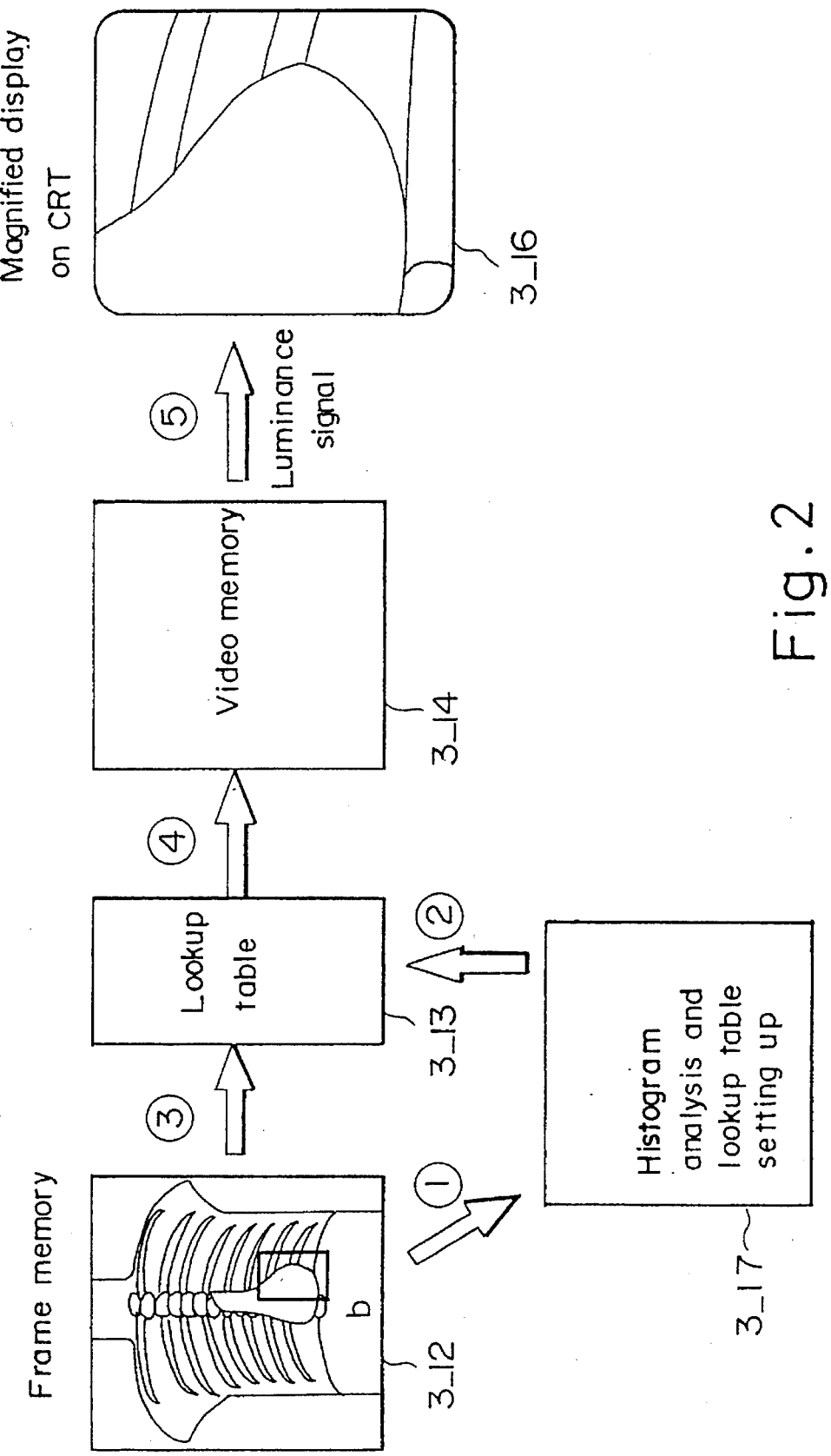
FIG. 2 is an illustration showing a characteristic part of the present invention in the radiation image information reader shown in FIG. 1.
Figure 15:
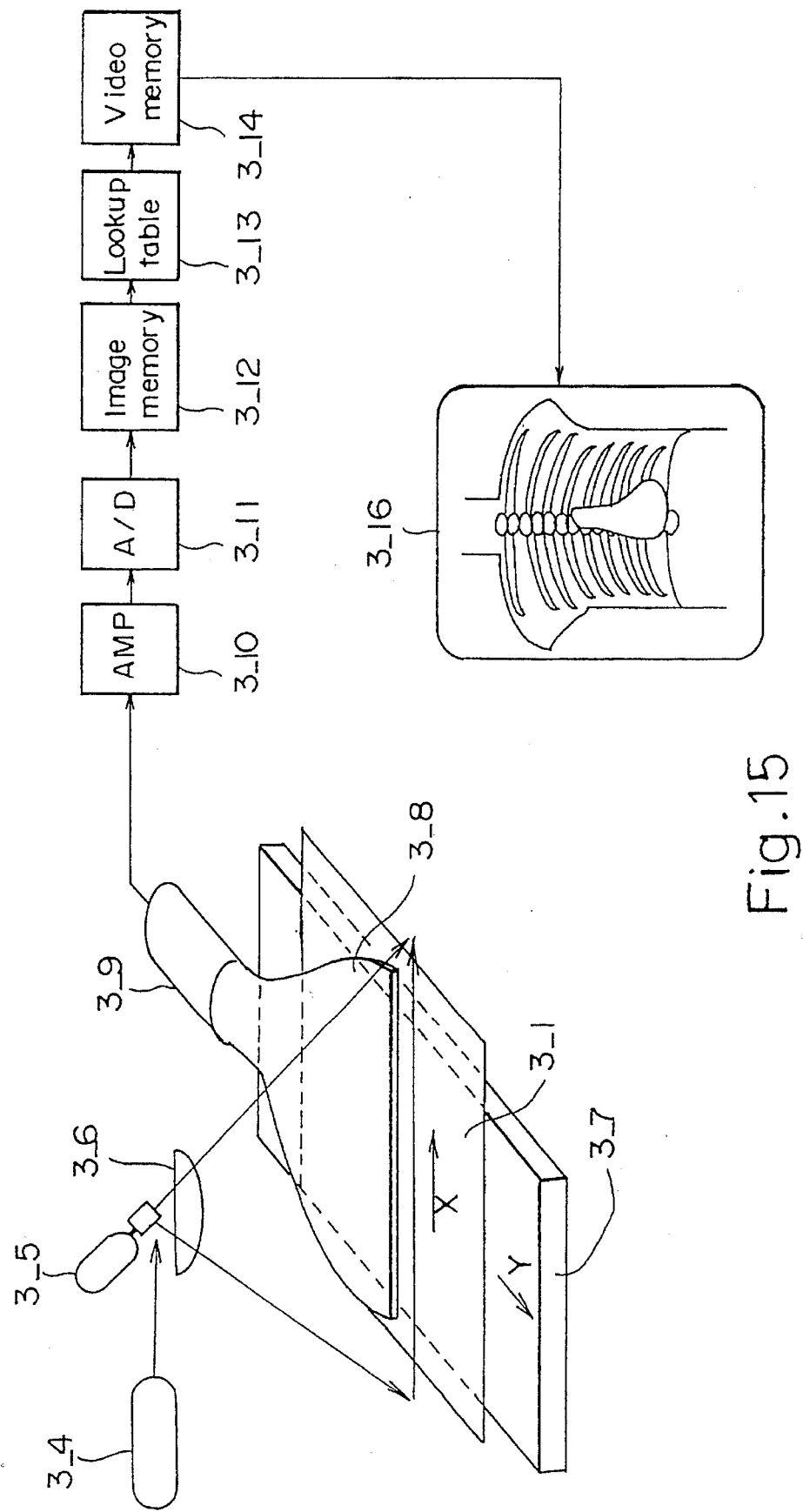
FIG. 15 is an approximate configuration of the conventional radiation image information reader.

FIG. 1 is an outlined configuration of a radiation image information reader in which the first embodiment of the present invention is involved. In this case, the same symbols as given in FIG. 5 are assigned to the same components as in the aforementioned conventional example (refer to FIG. 15) and the description which may be doubled is omitted. FIG. 2 is an illustration showing a characteristic part of the present invention in the radiation image information reader shown in FIG. 1 and FIGS. 3–5 are respectively a diagram showing an example method for obtaining the lookup table. Here, a thoracic (chest) X-ray image of a human body is described as an example.

In this embodiment, a histogram analysis and lookup table setting part 3-17 is provided as shown in FIGS. 1 and 2.

Figure 3A:
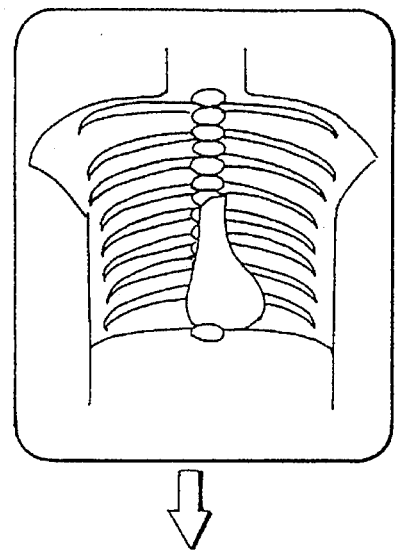
FIG. 3 is a diagram showing an example method for obtaining a lookup table.
Figure 3B:
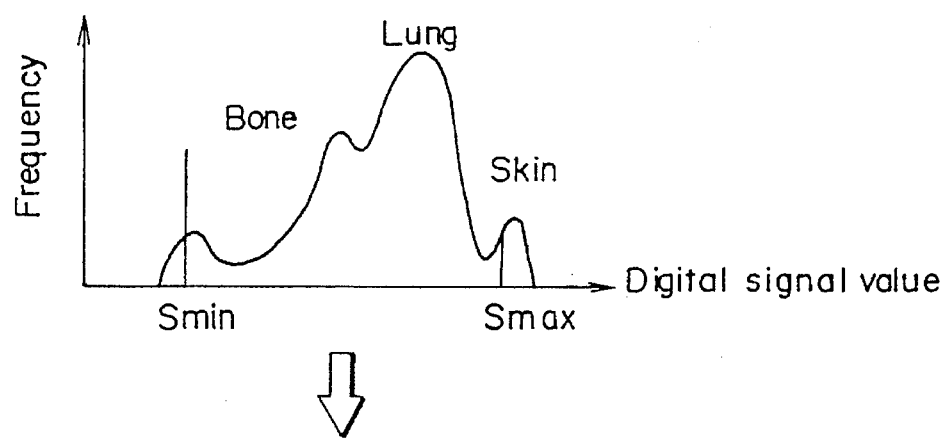
Figure 3C:
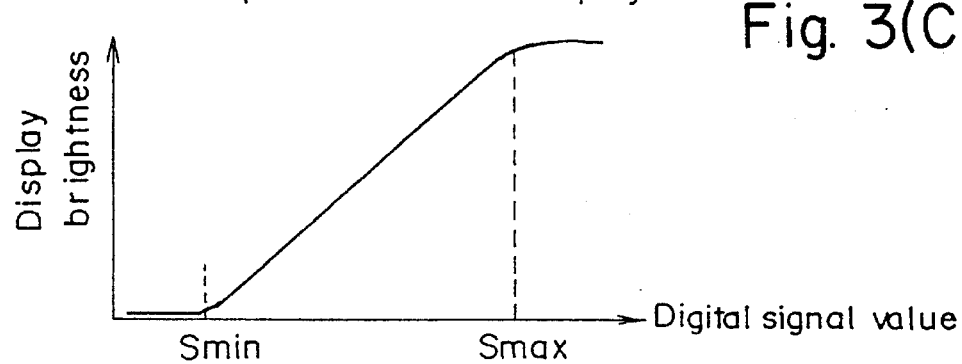
Figure 4A:
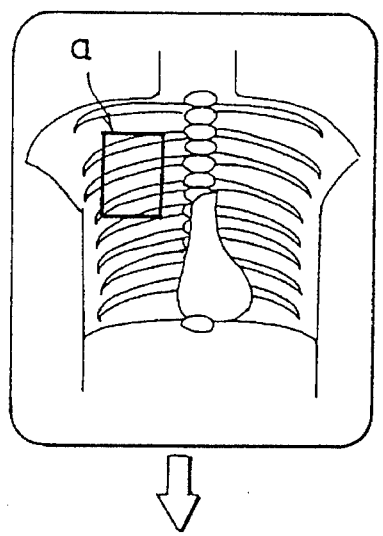
FIG. 4 is a diagram showing an example method for obtaining a lookup table.
Figure 4B:
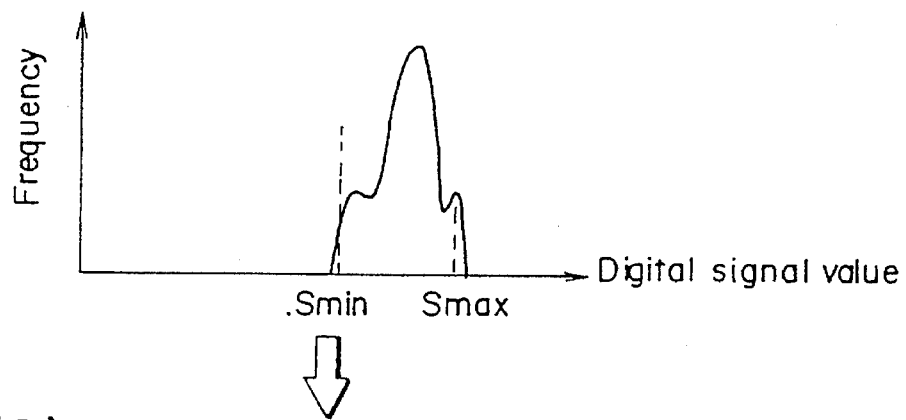
Figure 4C:
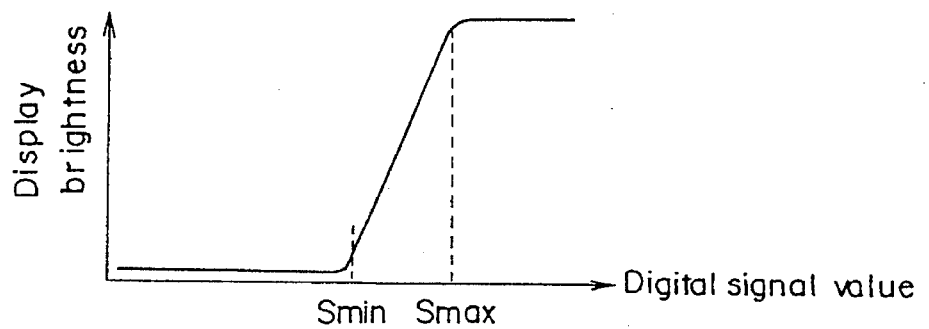

Pixel data corresponding to all or a partial area of the image to be displayed of the thoracic X-ray image stored in the image memory 3-12 is entered into this histogram analysis and lookup table setting part 3-17 and a histogram of pixel values of pixel data which has been entered is obtained. In other words, as shown in FIG. 3, for displaying the overall thoracic X-ray image, the pixel data corresponding to this overall image is entered to obtain the histogram. Similarly, for magnifying only the partial area of the thoracic X-ray image for display as shown in FIGS. 4 and 5, the pixel data corresponding to this partial area is entered to obtain the histogram.

In the histogram analysis and lookup table setting part 3-17, the conversion information is obtained according to the maximum value (Smax) and the minimum value (Smin) of the histogram, after the histogram has been obtained and the conversion information is set in the lookup table 3-13.

Subsequently, the pixel data corresponding to the partial area of the image, which have been used for histogram analysis in the histogram analysis and lookup table setting part 3-1, are read out from the frame memory 3-12 and converted according to the lookup table to the pixel data having the pixel values suited for display. Converted pixel data are entered into the video memory 3-14. The pixel data entered into this video memory 3-14 is converted to a luminance signal and an image based on this luminance signal is displayed on the CRT 3-16. It is easily understood that, for magnifying only the partial area of the image for display, appropriate interpolation is carried out in addition to conversion of the pixel data using the lookup table 3-14.

Figure 6:
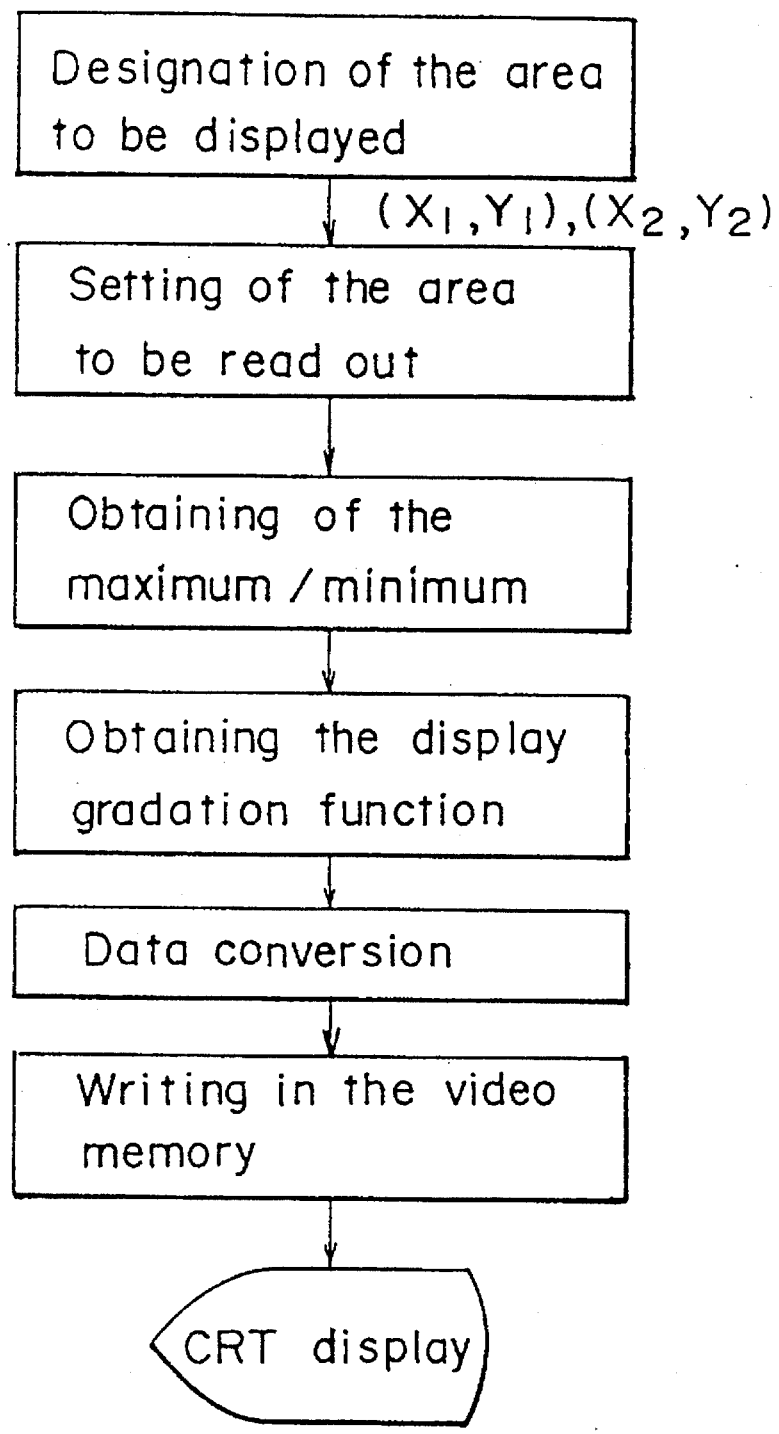
FIG. 6 is a flow chart of the second embodiment involved in the radiation image information reader for which the image displaying method according to the present invention is implemented in accordance with computer software.
Figure 7:
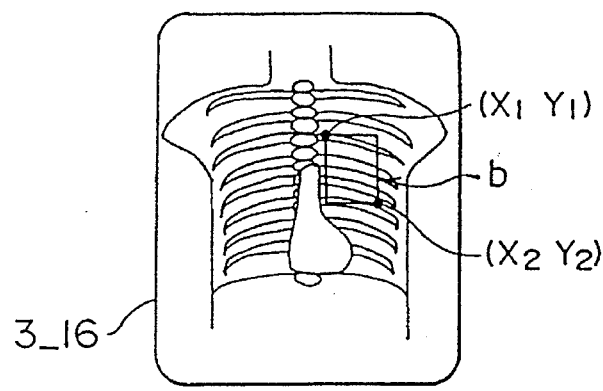
FIGS. 7(A)–(D) are illustrations of the second embodiment shown in FIG. 6.
Figure 7:
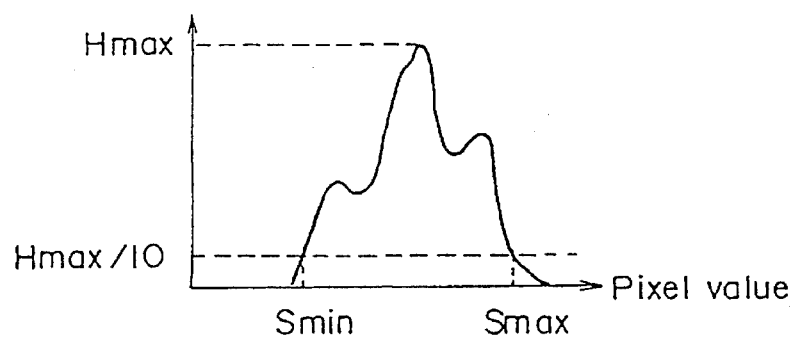
Figure 7:
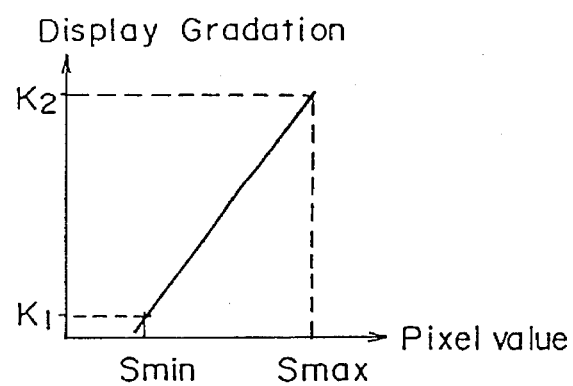
Figure 7:
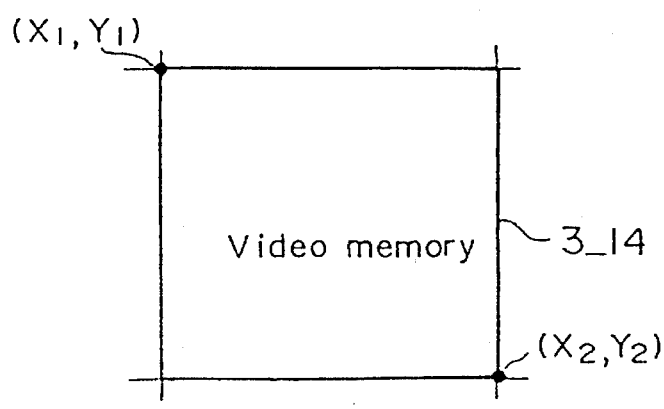

FIG. 6 is a flow chart of the second embodiment involved in the radiation image information reader for which the image displaying method in accordance with the present invention is implemented. FIG. 7 is an illustration of the above embodiment.

In the state where the overall image is displayed on the CRT 3-16, positional information entry means (not shown) such as a mouse or a track ball is operated by an observer of the image. The partial area b, with which the observer is concerned, is designated (refer to FIG. 6 Step (a) and FIG. 7).

As shown in FIG. 7 (a), the starting address of the partial area b shall be $(X_1, Y_1)$ and the ending address shall be $(X_2, Y_2)$ on the CRT 3-16.

With this designation of the partial area b, an area (the addresses of this area are referred to as addresses $(X_1, Y_1)$–$(X_2, Y_2)$) of the frame memory 3-12 (FIG. 1) in which the pixel data corresponding to the partial area b is stored is determined (FIG. 6 Step(b)). When the addresses $(X_1, Y_1)$–$(X_2, Y_2)$ of the frame memory 3-12 are determined as described above, the pixel data stored in these addresses $(X_1, Y_1)$–$(X_2, Y_2)$ is read out and a histogram of the pixel values of these pixel data is obtained as shown in FIG. 7 (B). When this histogram is obtained, the peak value HMAX of the histogram is obtained. An intersection with the histogram is obtained with 1/10 of the peak value $H_{MAX}$, that is, $H_{MAX}/10$ as a threshold, thereby obtaining the minimum value $S_{MIN}$ and the maximum value $S_{MAX}$ (FIG. 6 Step (c)).

Next, the minimum value $S_{MIN}$ and the maximum value $S_{MAX}$ obtained as described above are respectively correlated to the minimum value $K_1$ and the maximum value $K_2$ of the display gradation. The pixel data stored in the frame memory 3-12 is converted to the pixel data for display. Then, a display gradation function is obtained (refer to FIG. 7 (C)).

After this, the pixel data stored in addresses $(X_1, Y_1)$–$(X_2, Y_2)$ of the frame memory 3-12, that is, the pixel data corresponding to the partial area b shown in FIG. 7 (A), is read out, converted to the pixel data for display according to the read-out brightness conversion function (refer to FIG. 7(C)) obtained as described above (FIG. 6 Step (e)), given an interpolation processing as required and stored in the video memory 3-14.

This video memory 3-14 corresponds to the overall screen of the CRT 3-16. Therefore, as shown in FIG. 7 (D), the starting addresses and the ending addresses of the video memory 3-14 correspond to the starting addresses $(X_1, Y_1)$ and the ending addresses $(X_2, Y_2)$ of the partial area b shown in FIG. 7 (A). Subsequently, an image based on the pixel data stored in this video memory 3-14 is displayed on the CRT 3-16 (FIG. 6 Step (e)).

As shown in the second embodiment, the image conversion method according to the present invention can also be implemented with computer software.

Figure 8:
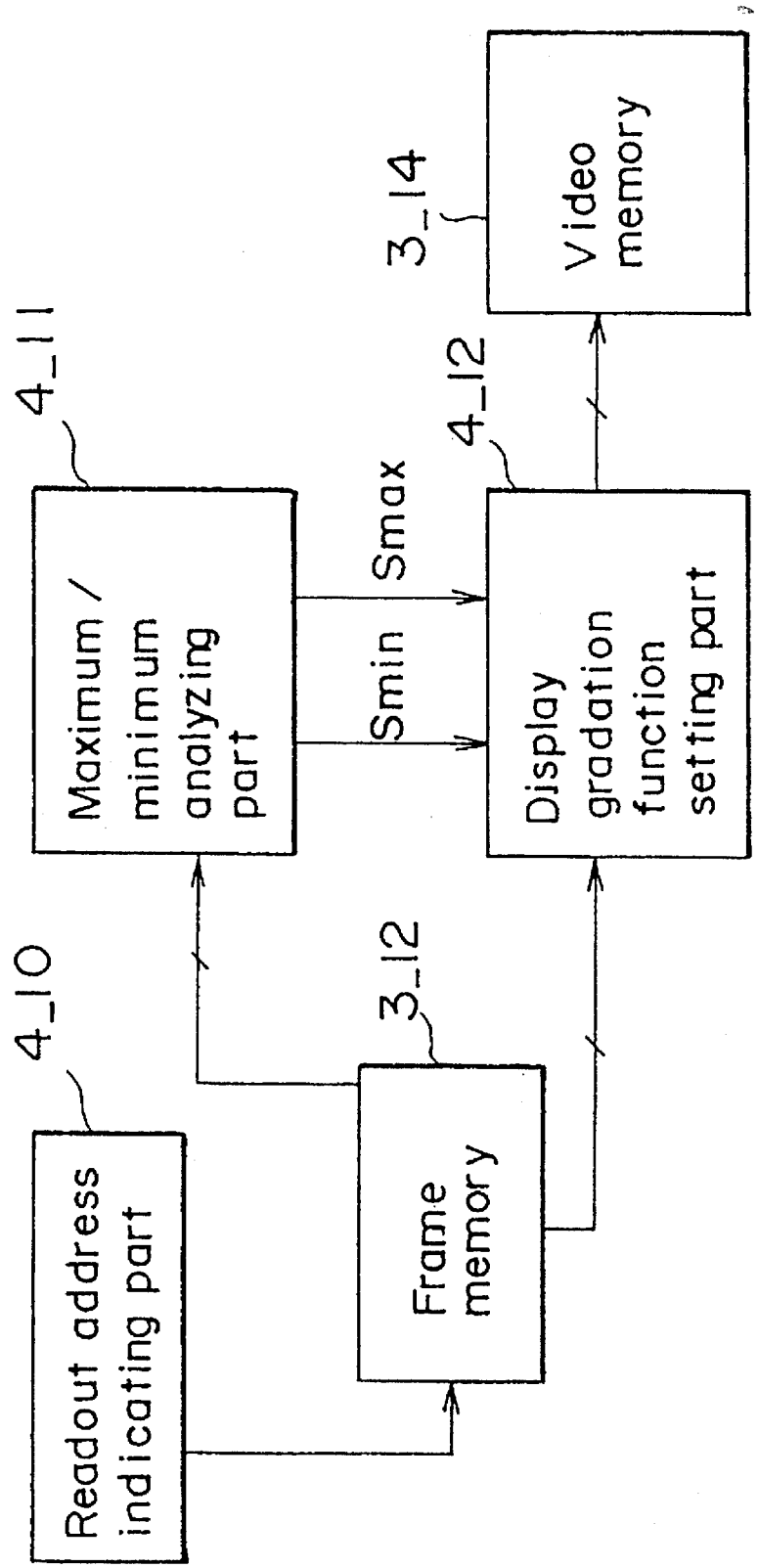
FIG. 8 is a block diagram of the third embodiment involved in the radiation image information reader for which the image displaying method according to the present invention is implemented with hardware.

FIG. 8 is a block diagram of the third embodiment involved in the radiation image information reader for which the image displaying method in accordance with the present invention is implemented with hardware.

When a partial area of the overall image displayed on the CRT 3-16 (refer to FIG. 1) by the positional information entry means which is not shown, is designated, addresses $(X_1, Y_1)$~$(X_2, Y_2)$ of the frame memory 3-12 where the pixel data corresponding to the designated partial area is stored are obtained from the readout address indicating part 4-10. The pixel data stored in addresses $(X_1, Y_1)$~$(X_2, Y_2)$ of the frame memory 3-12 is read out in accordance with an indication by this readout address indicating part 4-10 and entered into the maximum/minimum analyzing part 4-11.

Figure 9:
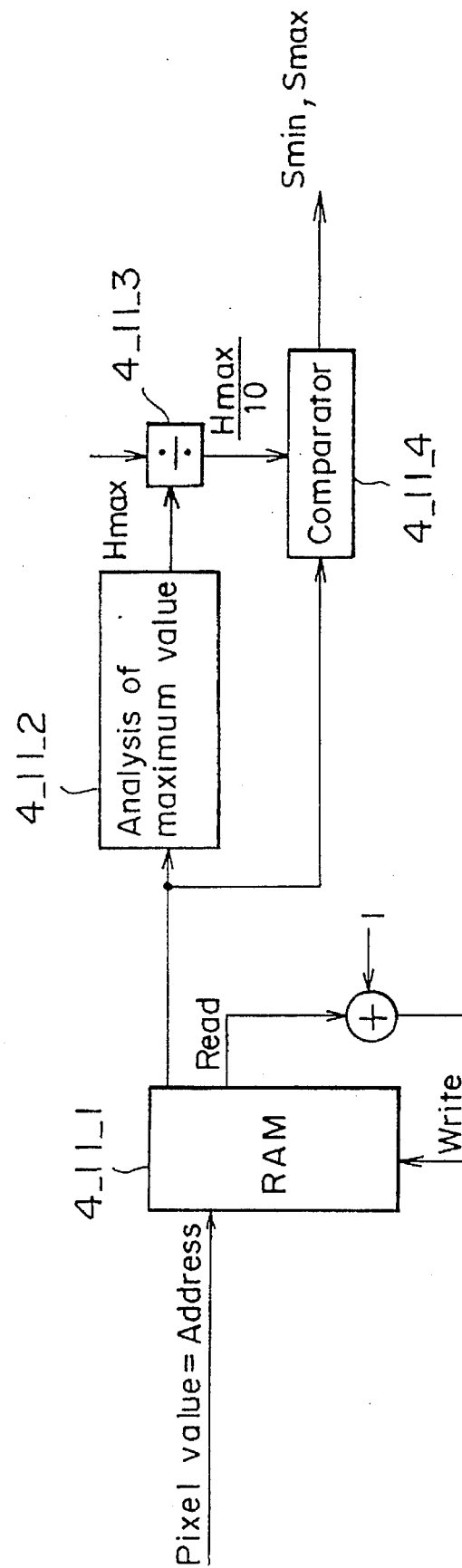
FIG. 9 is a diagram showing a circuit configuration of the maximum/minimum analyzing part 4-11.

FIG. 9 shows a circuit configuration of the maximum/minimum analyzing part 4-11.

The maximum/minimum analyzing part 4-11 is provided with a RAM (Random Access Memory) 4-11-1 where a process for reading out the values stored in the addresses corresponding to the pixel values of pixel data read out from the frame memory 3-12, after initializing all values stored in the memory areas of the addresses to "0"; adding "1" to the readout values; and writing them in the same addresses is carried out. With this processing, a histogram of the readout pixel data is formed in the RAM 4-11-1 when the reading of the pixel data stored in addresses $(X_1, Y_1)$~$(X_2, Y_2)$ of the frame memory 3-12 is finished. When the histogram of pixel data is thus formed in the RAM 4-11-1, the values of the histogram stored in the addresses of the RAM 4-11-1 are read out in sequence and entered into the maximum value analyzing circuit 4-11-2.

In the maximum value analyzing circuit 4-11-2, the maximum value (peak value) $H_{MAX}$ of histogram values entered is obtained. In a divider 4-11-3, this maximum value $H_{MAX}$ is divided by a specified value ('10' in this case) and a threshold $H_{MAX}/10$ is obtained. This threshold $H_{MAX}/10$ is entered into a comparator 4-11-4.

Histogram values are read out again in sequence from the RAM 4-11-1 and entered into the comparator 4-11-4. Then, histogram values are compared with the threshold $H_{MAX}/10$. The minimum value $S_{MIN}$ and the maximum value $S_{MAX}$ of the pixel data are then obtained. The minimum value SMIN and the maximum value $S_{MAX}$ which are thus obtained are entered into the display gradation function setting part 4-12.

Figure 10:
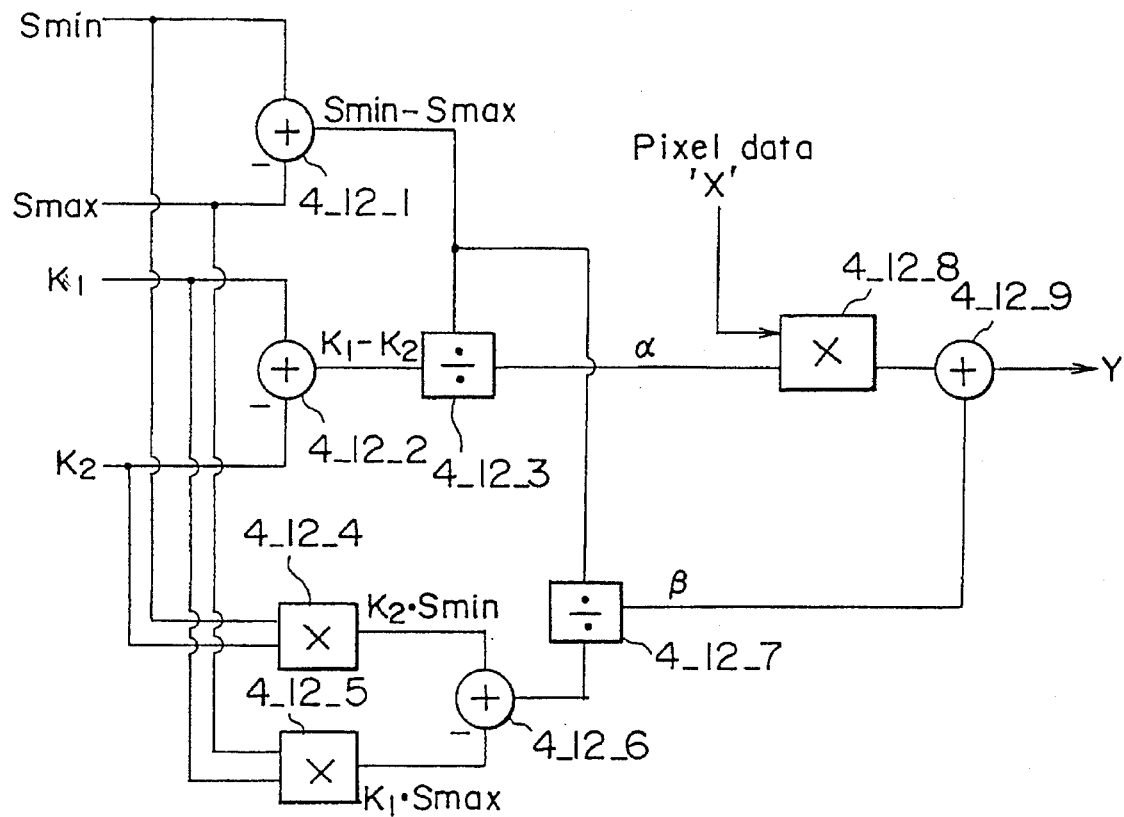
FIG. 10 is a diagram showing a circuit configuration of the display gradation function setting part 4-12.
Figure 11:
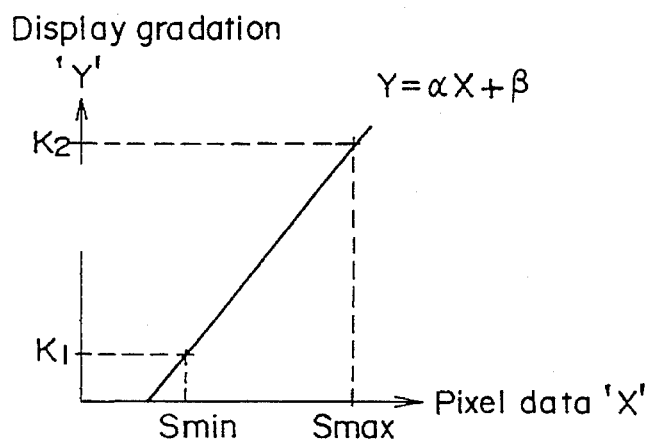
FIG. 11 is a diagram showing display gradation functions obtained at the display gradation function setting part 4-12.

FIG. 10 shows a circuit configuration of the display gradation function setting part 4-12 and FIG. 11 shows the display gradation functions to be obtained from the display gradation function setting part 4-12. In the display gradation function setting part 4-12 shown in FIG. 10, a display gradation function $Y=\alpha X+\beta$ is obtained so that the minimum value $S_{MIN}$ and the maximum value $S_{MAX}$ of pixel data are respectively correlated to the minimum value $K_1$ and the maximum value $K_2$ of the display gradation, and the pixel data is read out from the frame memory 3-12 according to this display gradation function $Y=\alpha X+\beta$. The designation from the readout address indicating part 4-10 shown in FIG. 8 and the pixel data 'X' corresponding to the designated partial area is converted to the pixel data 'Y' for display.

As shown in FIG. 10, the minimum value $S_{MIN}$ and the maximum value $S_{MAX}$ of pixel data obtained in the maximum/minimum analyzing part 4-11 and the minimum value K1 and the maximum value K2 of the display gradation which are determined with the characteristics of the CRT 3-16 are entered into the display gradation function setting part 4-12. Then, a coefficient $\alpha$ is obtained by two subtracters 4-12-1 and 4-12-2 and the divider 4-12-3. Also, a coefficient $\beta$ is obtained by two multipliers 4-12-4 and 4-12-5, subtracter 4-12-6 and divider 4-12-7. The coefficient $\alpha$ obtained is entered into a multiplier 4-12-8 and multiplied with the pixel data 'X' read out from the frame memory 3-12, and the coefficient $\beta$ is entered into an adder 4-12-9 and added to the multiplication effect $\alpha \cdot X$. Therefore a display gradation 'Y' is obtained as $Y=\alpha \cdot X+\beta$. The pixel data which is thus converted to the display gradation is entered into the video memory 3-14. A magnified image of the partial area designated according to the pixel data entered into this video memory 3-14 is displayed on the full screen of the CRT 3-16. The magnified image displayed on the CRT 3-16 is an image based on the pixel data which are brightness-converted according to the histogram of only the partial area and can therefore be displayed with an appropriate brightness.

Figure 12:
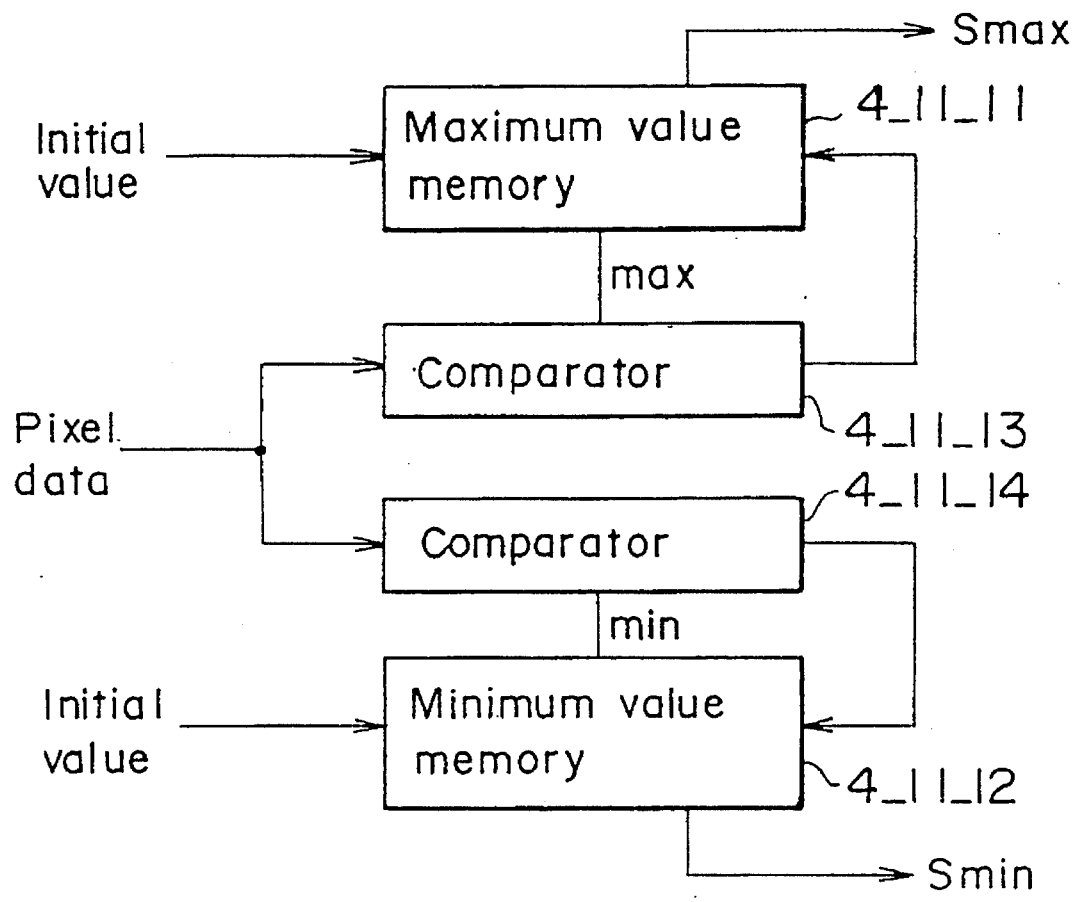
FIG. 12 is a diagram showing a circuit configuration which differs from that shown in FIG. 9 of the maximum/minimum analyzing part 4-11 shown in FIG. 8.

FIG. 12 shows a circuit configuration of the maximum/minimum analyzing part 4-11 shown in FIG. 8, differing from that shown in FIG. 9.

In the maximum value memory 4-11-11 and the minimum value memory 4-11-12, the minimum value $S_{MIN}$ and the maximum value $S_{MAX}$ of pixel data are stored after the calculation result is obtained. Additionally, the absolute minimum value (value '0' in this case) and the absolute maximum value (value '4096' in this case) within the range where these values are expressed as the pixel values of pixel data in this system are stored as the initial values. Subsequently, the pixel data corresponding to the partial areas which are designated in sequence, are entered from the frame memory 3-12 into comparators 4-11-13 and 4-11-14 and compared with the contents stored in the maximum value memory 4-11-1 and the minimum value memory 4-11-2. When the pixel value of pixel datum entered is greater than the contents stored in the maximum value memory 4-11-1, this pixel datum is stored in the maximum value memory 4-11-1. Similarly, when the pixel value of pixel datum entered is smaller than the contents of the minimum value memory 4-11-2, this pixel datum is stored in the minimum value memory 4-11-2. The above calculation is repeated every time pixel data is entered. When all pixel data corresponding to the designated partial area is thus read out from the frame memory 3-12, the maximum value $S_{MAX}$ and the minimum value $S_{MIN}$ of pixel data corresponding to the partial area are stored in the maximum value memory 4-11-1 and the minimum value memory 4-11-2, respectively. The maximum value $S_{MAX}$ and the minimum value $S_{MIN}$ of pixel data thus obtained are entered into the display gradation function setting part 4-12 shown in FIG. 8.

Figure 13:
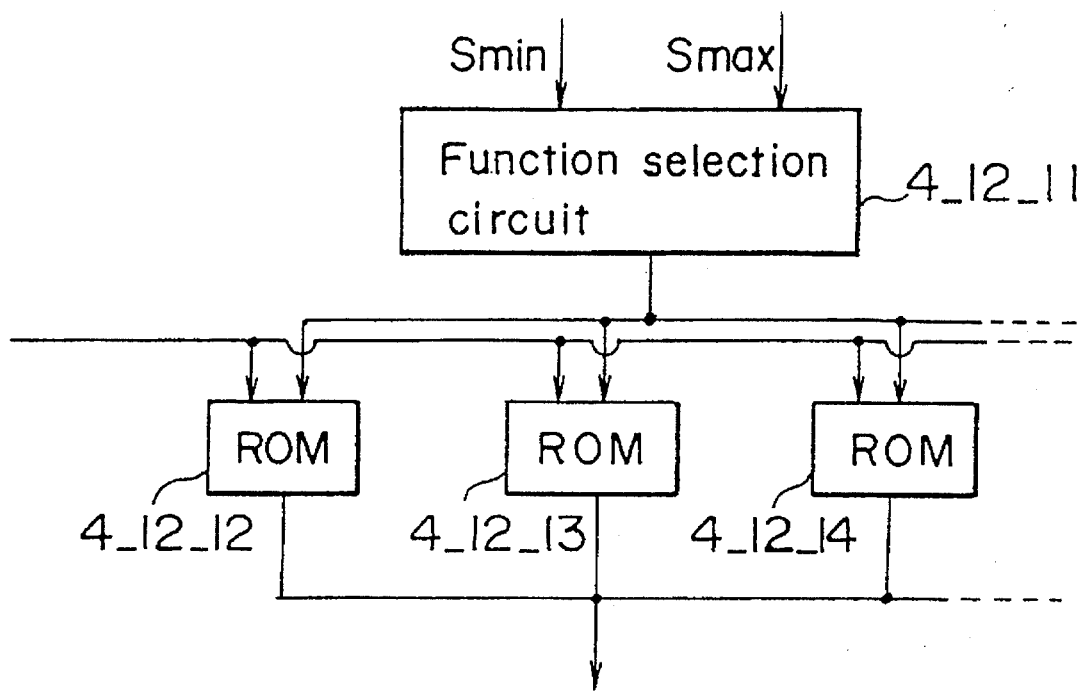
FIG. 13 is a diagram showing a circuit configuration which differs from that shown in FIG. 10 of the display gradation function setting part 4-12 shown in FIG. 8.

FIG. 13 shows a circuit configuration of the display gradation function setting part 4-12 shown in FIG. 8, differing from that shown in FIG. 10.

Figure 14:
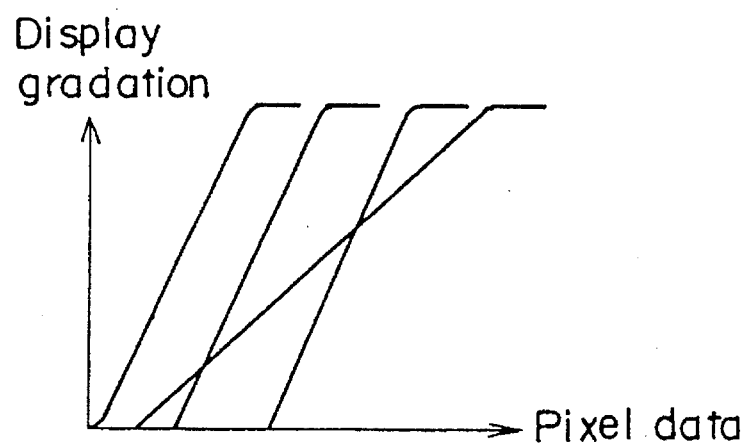
FIG. 14 is a diagram graphically showing the conversion table for converting pixel data which is stored in respective ROMs (Read Only Memory) and read out from the frame memory 3-12 to pixel data for display.

FIG. 14 graphically shows a conversion table stored in each ROM (Read Only Memory) for converting the pixel data read out from the frame memory 3-12 to the pixel data for display.

The maximum value $S_{MAX}$ and the minimum value $S_{MIN}$ of pixel data obtained in the maximum/minimum analyzing part 4-11 are entered into a function selection circuit 4-12-11. In this function selection circuit 4-12-11, one of a plurality of ROMs 4-12-12, 4-12-13, 4-12-14, . . . is selected according to the maximum value $S_{MAX}$ and the minimum value $S_{MIN}$ of pixel data which have been entered. The criteria for selecting one of ROMs 4-12-12, 4-12-13, 4-12-14, . . . is not specifically limited. However, in the function selection circuit 4-12-11, for example, the maximum value $S_{max}$—the minimum value $S_{MIN}$ and (the maximum value $S_{max}$ + the minimum value $S_{MIN})/2$ are obtained. One ROM is then selected in accordance with these two values obtained.

When one ROM is thus selected in the function selection circuit 4-12-11, the pixel values of pixel data read out from the frame memory 3-12 are entered as addresses into the selected ROM and the display gradation stored in this ROM is entered from the ROM into the video memory 3-14. A magnified image with an appropriate brightness distribution can be obtained by such machine.

As known from the descriptions of the above described embodiments, the present invention is not limited to the embodiments described above.

I claim:

1. An image displaying method comprising the steps of:

storing a plurality of first pixel data, respectively corresponding to a plurality of pixel values which form an image;

obtaining second pixel data by reading out said first pixel data and converting said plurality of pixel values of said first pixel data to a plurality of second pixel values for display;

displaying said image based on said second pixel data, wherein said first pixel data corresponding to a partial area of said image are read out for displaying a partial image corresponding to said partial area of the image, conversion information for converting said first pixel data to said second pixel data in accordance with said first pixel data which has been read out, said first pixel data corresponding to said partial area being converted to said second pixel data in accordance with said conversion information, and an image corresponding to said partial area displayed in accordance with said second pixel data.

2. An image displaying method in accordance with claim 1, wherein a method for obtaining said conversion information comprises:

obtaining a histogram of pixel values of said first pixel data; and obtaining said conversion information according to said histogram.

3. An image displaying method in accordance with claim 1, wherein said conversion information is a conversion formula.

4. An image displaying method in accordance with claim 1, wherein said conversion information is a conversion table.

5. An image displaying method in accordance with claim 4, wherein said conversion table is a lookup table.

6. An image displaying method in accordance with claim 1, wherein said first pixel data is obtained by reading said image from an accelerated phosphorescence fluorescent material in which said image is accumulated.

7. An image displaying method comprising the steps of:

storing a plurality of first pixel data, respectively corresponding to a plurality of pixel values which form an image;

reading the plurality of first pixel data corresponding to a partial area of the image designated by an external source;

obtaining conversion information for converting the first pixel data to the second pixel data in accordance with the read first pixel data;

converting the first pixel data corresponding to the partial area of the image in accordance with the above conversion information, to obtain second pixel data; and displaying an image corresponding to the partial area in accordance with the second pixel data.

8. An image displaying method as recited in claim 7, wherein said external source is an operator.

9. An image displaying method in accordance with claim 7, wherein a method for obtaining said conversion information comprises:

obtaining a histogram of pixel values of said first pixel data; and obtaining said conversion information according to said histogram.

10. An image displaying method in accordance with claim 7, wherein said conversion information is a conversion formula.

11. An image displaying method in accordance with claim 7, wherein said conversion information is a conversion table.

12. An image displaying method in accordance with claim 11, wherein said conversion table is a lookup table.

13. An image displaying method in accordance with claim 7, wherein said first pixel data is obtained by reading said image from an accelerated phosphorescence fluorescent material in which said image is accumulated.

* * * * *

UNITED STATES PATENT AND TRADEMARK OFFICE
CERTIFICATE OF CORRECTION

PATENT NO. : 5,617,313
DATED : April 1, 1997
INVENTOR(S) : Fumihiro NAMIKI

It is certified that error appears in the above-indentified patent and that said Letters Patent is hereby corrected as shown below:

Column 2, line 40, "3-12" should be --3-14--.

Column 9, line 9, through Column 10, line 41 should be deleted in their entirety and replaced with the following:

--1. An image displaying method comprising the steps of:

(a) storing first pixel data;

(b) converting the first pixel data to first pixel values forming an initial image, using first conversion information determined from the first pixel data;

(c) displaying the initial image in accordance with the first pixel values;

(d) obtaining second pixel data by reading out a portion of the first pixel data corresponding to a partial area of the initial image displayed in step (c);

(e) converting the second pixel data to second pixel values for an enlarged image corresponding to the partial area of the initial image, using second conversion information determined from the second pixel data; and (f) displaying the enlarged image corresponding to the partial area in accordance with the second pixel values.

UNITED STATES PATENT AND TRADEMARK OFFICE
CERTIFICATE OF CORRECTION

PATENT NO. : 5,617,313
DATED : April 1, 1997
INVENTOR(S) : Fumihiro NAMIKI

It is certified that error appears in the above-indentified patent and that said Letters Patent is hereby corrected as shown below:

2. An image displaying method in accordance with claim 1, further comprising the step of (g) obtaining the second conversion information used in step (d) by:

(g1) obtaining a histogram of the second pixel data; and (g2) obtaining the second conversion information according to the histogram.

3. An image displaying method in accordance with claim 1, further comprising the step of (g) obtaining the second conversion information as a conversion formula.

4. An image displaying method in accordance with claim 1, further comprising the step of (g) obtaining the second conversion information as a conversion table.

5. An image displaying method in accordance with claim 1, wherein the conversion table is a lookup table.

UNITED STATES PATENT AND TRADEMARK OFFICE
CERTIFICATE OF CORRECTION

PATENT NO. : 5,617,313
DATED : April 1, 1997
INVENTOR(S) : Fumihiro NAMIKI

It is certified that error appears in the above-indentified patent and that said Letters Patent is hereby corrected as shown below:

6. An image displaying method in accordance with claim 1, wherein the first pixel data is obtained by reading from an accelerated phosphorescence fluorescent material in which a generated image is accumulated.

7. An image displaying method comprising the steps of:
 (a) storing first pixel data;
 (b) converting the first pixel data to first pixel values forming a first image, using first conversion information determined from the first pixel data;
 (c) displaying the first image in accordance with the first pixel values;
 (d) reading a portion of the first pixel data corresponding to a partial area of the first image designated by an external source to obtain second pixel data;
 (c) obtaining second conversion information for converting the second pixel data to [the] second pixel values in accordance with the second pixel data;
 (d) converting the second pixel data in accordance with the second conversion information, to obtain second pixel values; and

UNITED STATES PATENT AND TRADEMARK OFFICE
CERTIFICATE OF CORRECTION

PATENT NO. : 5,617,313
DATED : April 1, 1997
INVENTOR(S) : Fumihiro NAMIKI

It is certified that error appears in the above-indentified patent and that said Letters Patent is hereby corrected as shown below:

(e) displaying a second image corresponding to the partial area in accordance with the second pixel values.

8. An image displaying method as recited in claim 7, wherein the external source is a human operator.

9. An image displaying method in accordance with claim 7, wherein said obtaining of the second conversion information in step (c) comprises the steps of:

(c1) obtaining a histogram of the second pixel data; and (c2) obtaining the second conversion information according to the histogram.

10. An image displaying method in accordance with claim 7, wherein said obtaining in step (c) obtains the second conversion information as a conversion formula.

11. An image displaying method in accordance with claim 7, wherein said obtaining in step (c) obtains the second conversion information in a conversion table.

UNITED STATES PATENT AND TRADEMARK OFFICE
CERTIFICATE OF CORRECTION

PATENT NO.  : 5,617,313
DATED       : April 1, 1997
INVENTOR(S) : Fumihiro NAMIKI It is certified that error appears in the above-indentified patent and that said Letters Patent is hereby corrected as shown below:

12. An image displaying method in accordance with claim 11, wherein said conversion table is a lookup table.

13. An image displaying method in accordance with claim 7, wherein the first pixel data is obtained by reading a generated image from an accelerated phosphorescence fluorescent material in which the generated image is accumulated.--

Signed and Sealed this

Twenty-ninth Day of July, 1997

Attest:

BRUCE LEHMAN

*Attesting Officer*         Commissioner of Patents and Trademarks